(12) United States Patent
Parra

(10) Patent No.: US 10,676,931 B2
(45) Date of Patent: Jun. 9, 2020

(54) ADJUSTABLE APPARATUS FOR WATER CAPTURE

(71) Applicant: Alvin Parra, South Pasadena, CA (US)

(72) Inventor: Alvin Parra, South Pasadena, CA (US)

( * ) Notice: Subject to any disclaimer, the term of this patent is extended or adjusted under 35 U.S.C. 154(b) by 0 days.

(21) Appl. No.: 16/206,918

(22) Filed: Nov. 30, 2018

(65) Prior Publication Data

US 2019/0161974 A1 May 30, 2019

Related U.S. Application Data

(60) Provisional application No. 62/592,407, filed on Nov. 30, 2017.

(51) Int. Cl.
| | |
|---|---|
| *E04D 13/068* | (2006.01) |
| *A47K 1/00* | (2006.01) |
| *F16L 37/48* | (2006.01) |
| *A61M 31/00* | (2006.01) |
| *A47K 3/28* | (2006.01) |
| *E03C 1/00* | (2006.01) |
| *E03B 1/04* | (2006.01) |
| *E04D 13/064* | (2006.01) |
| *E04D 13/072* | (2006.01) |
| *E03D 1/00* | (2006.01) |
| *E03C 1/04* | (2006.01) |

(52) U.S. Cl.
CPC ............ *E04D 13/0685* (2013.01); *A47K 1/00* (2013.01); *A47K 3/281* (2013.01); *A61M 31/00* (2013.01); *E03B 1/048* (2013.01); *E03C 1/00* (2013.01); *F16L 37/48* (2013.01); *E03C 1/0408* (2013.01); *E03D 1/003* (2013.01); *E04D 13/0645* (2013.01); *E04D 13/0727* (2013.01)

(58) Field of Classification Search
CPC ............ E04D 16/0685; E04D 13/0645; E04D 13/0727; A47K 1/00; A47K 3/281; A61M 31/00; E03B 1/048; E03C 1/00; E03C 1/0408; F16L 37/48; E03D 1/003
USPC .............................................................. 4/605
See application file for complete search history.

(56) References Cited

U.S. PATENT DOCUMENTS

| | | | | |
|---|---|---|---|---|
| 2,539,976 A | * | 1/1951 | Samson ................ | A47K 3/281 239/511 |
| 3,847,159 A | * | 11/1974 | Hofer ..................... | B05B 1/267 239/507 |

(Continued)

OTHER PUBLICATIONS

International Application No. PCT/US18/63471, Notification of transmittal of international search report and the written opinion of the international search authority, or the declaration, dated Feb. 5, 2019.

*Primary Examiner* — Benjamin R Shaw
(74) *Attorney, Agent, or Firm* — Kunzler Bean & Adamson, PC

(57) ABSTRACT

Apparatuses, systems, and methods are disclosed for water capture. A water collection opening is shaped to collect water from a water source. A water outlet is in fluid communication with a water collection opening to receive collected water from a water source through the water collection opening. A horizontal adjustment mechanism is configured to provide mechanical support to a water outlet and a water collection opening at any one of a plurality of user selectable positions at different horizontal offsets relative to a water source to accommodate different sizes and types of water sources.

18 Claims, 8 Drawing Sheets

(56) References Cited

U.S. PATENT DOCUMENTS

| | | | | |
|---|---|---|---|---|
| 4,784,184 | A * | 11/1988 | Gates | E03C 1/086 |
| | | | | 138/109 |
| 5,165,456 | A * | 11/1992 | Woolman | E03B 1/048 |
| | | | | 141/98 |
| 5,241,714 | A * | 9/1993 | Barry | A61M 3/0208 |
| | | | | 4/605 |
| 5,862,544 | A * | 1/1999 | Placencia | E03C 1/02 |
| | | | | 4/597 |
| 9,074,356 | B2 | 7/2015 | Tarantino | |
| 9,663,924 | B2 * | 5/2017 | Turner | E03B 1/042 |
| 2009/0082729 | A1 * | 3/2009 | Callow | A61M 31/00 |
| | | | | 604/150 |
| 2009/0173388 | A1 * | 7/2009 | Sever | E03C 1/08 |
| | | | | 137/1 |
| 2009/0288246 | A1 * | 11/2009 | Sanaghan, Jr. | E03D 1/003 |
| | | | | 4/415 |
| 2013/0048104 | A1 * | 2/2013 | Li | E03B 1/048 |
| | | | | 137/386 |
| 2013/0061944 | A1 * | 3/2013 | Tarantino | E03B 1/042 |
| | | | | 137/101.27 |
| 2016/0326729 | A1 * | 11/2016 | Jones | E03C 1/023 |
| 2017/0181583 | A1 * | 6/2017 | Chiu | B05B 14/40 |
| 2017/0260721 | A1 * | 9/2017 | Velez, Jr. | E03C 1/0408 |
| 2017/0332564 | A1 * | 11/2017 | Wales | B67C 11/00 |
| 2018/0202135 | A1 * | 7/2018 | Chiu | E03B 1/048 |

* cited by examiner

ADJUSTABLE APPARATUS FOR WATER CAPTURE

CROSS-REFERENCES TO RELATED APPLICATIONS

This application claims the benefit of U.S. Provisional Patent Application No. 62/592,407 entitled "ADJUSTABLE APPARATUS FOR WATER CAPTURE" and filed on Nov. 30, 2017 for Alvin Parra, which is incorporated herein by reference in its entirety for all purposes.

FIELD

This present disclosure, in various embodiments, relates to water capture and more particularly relates to an apparatus for water capture with adjustable positioning.

BACKGROUND

Periodic drought, population increase, climate change, or the like can cause water shortages. Even when not experiencing water shortage conditions, conserving water can be responsible and/or may save money.

SUMMARY

Apparatuses are presented for water capture. In one embodiment, a water collection opening is shaped to collect water from a water source. A water outlet, in certain embodiments, is in fluid communication with a water collection opening to receive collected water from a water source through the water collection opening. In a further embodiment, a horizontal adjustment mechanism is configured to provide mechanical support to a water outlet and a water collection opening at any one of a plurality of user selectable positions at different horizontal offsets relative to a water source (e.g., to accommodate different sizes and/or types of water sources, or the like).

Other apparatuses are presented for water capture. In one embodiment, an apparatus includes means for collecting water from a water source. An apparatus, in a further embodiment, includes means for storing collected water from a water source for reuse. An apparatus, in some embodiments, includes means for providing mechanical support to a means for collecting water at any one of a plurality of user selectable positions at different horizontal offsets relative to a water source (e.g., to accommodate different sizes and/or types of water sources, or the like).

Systems are presented for water capture. In one embodiment, a conical water collection opening is positionable to collect water from a showerhead. A water outlet, in some embodiments, is in fluid communication with a conical water collection opening, receiving collected water from a showerhead through the conical water collection opening. In a further embodiment, a horizontal adjustment mechanism provides mechanical support to a water outlet and a conical water collection opening at any one of a plurality of user selectable positions at different horizontal offsets relative to a showerhead. In certain embodiments, a vertical adjustment mechanism is coupled to a water source on one end of the vertical adjustment mechanism with a horizontal adjustment mechanism extending from an opposite end of the vertical adjustment mechanism. A radial adjustment mechanism, in one embodiment, is configured to rotatably couple a horizontal adjustment mechanism to an opposite end of a vertical adjustment mechanism so that the horizontal adjustment mechanism is radially rotatable around an axis of the radial adjustment mechanism.

BRIEF DESCRIPTION OF THE DRAWINGS

In order that the advantages of the disclosure will be readily understood, a more particular description of the disclosure briefly described above will be rendered by reference to specific embodiments that are illustrated in the appended drawings. Understanding that these drawings depict only typical embodiments of the disclosure and are not therefore to be considered to be limiting of its scope, the subject matter of the present application will be described and explained with additional specificity and detail through the use of the accompanying drawings, in which.

DETAILED DESCRIPTION

Reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise.

Furthermore, the described features, structures, or characteristics of the disclosure may be combined in any suitable manner in one or more embodiments. In the following description, numerous specific details are disclosed to provide a thorough understanding of embodiments of the disclosure. One skilled in the relevant art will recognize, however, that the disclosure may be practiced without one or more of the specific details, or with other methods, components, materials, and so forth. In other instances, well-known structures, materials, or operations are not shown or described in detail to avoid obscuring aspects of the disclosure.

In the following description, certain terms may be used such as "up," "down," "upper," "lower," "horizontal," "vertical," "left," "right," and the like. These terms are used, where applicable, to provide some clarity of description when dealing with relative relationships. However, these terms are not intended to imply absolute relationships, positions, and/or orientations. For example, with respect to an object, an "upper" surface can become a "lower" surface simply by turning the object over. Nevertheless, it is still the same object.

Figure 1:
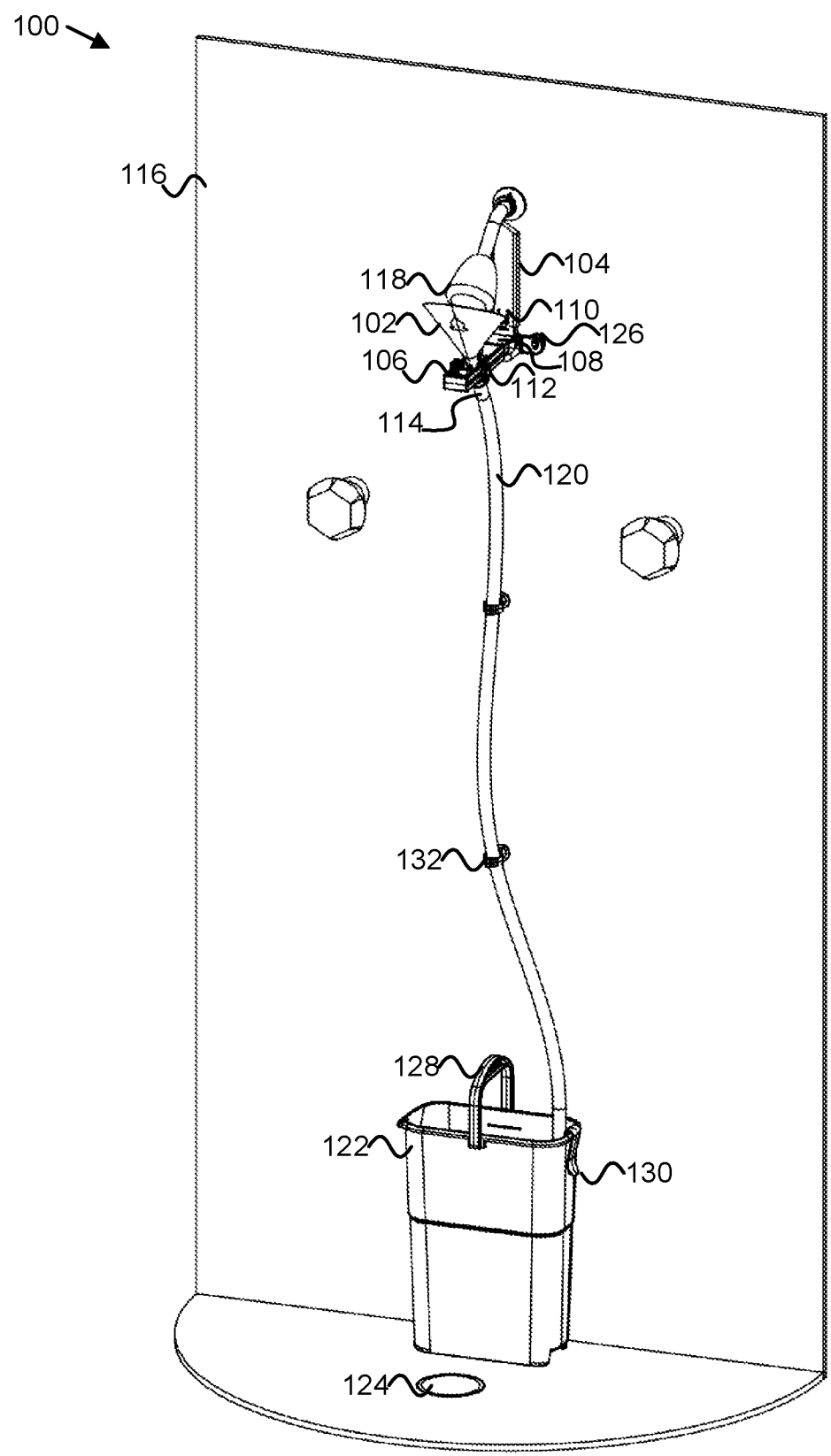
FIG. 1 is a schematic block diagram illustrating one embodiment of a system comprising an adjustable apparatus for water capture.

FIG. 1 depicts one embodiment of an adjustable apparatus 100 for water capture. In the depicted embodiment, the apparatus 100 includes one or more of a water collection opening 102 in fluid communication with a water outlet 114, a vertical adjustment mechanism 104, a horizontal adjustment mechanism 106, a radial adjustment mechanism 108, a vertical locking mechanism 110, and/or an angle locking mechanism 112.

In general, the apparatus 100 may be installable and/or positionable relative to a showerhead 118, a water faucet 118, and/or another water source 118 to capture waste water, gray water, or the like. For example, the apparatus 100 may collect, capture, and/or store water from a showerhead 118 while the water is warming up, before a user begins taking a shower. Instead of simply wasting water by letting it run down the drain 124, the apparatus 100 may conserve the water for other uses, such as watering plants, flushing a toilet, or the like. Showerheads 118, water faucets 118, and/or other water sources 118 may vary in size, shape, and/or position. In certain embodiments, the apparatus 100 may be adjustable in one or more directions for variable, configurable placement with regard to multiple types, sizes, positions, and/or shapes of showerheads 118, water faucets 118, and/or other water sources 118.

In one embodiment, the water collection opening 102 comprises a concave chamber with an opening facing toward a water faucet 118 or other water source 118, such as a showerhead 118 or the like, to receive and capture sprayed water. The water collection opening 102 may comprise a funnel, a cone, or the like with a wider opening narrowing to a smaller water outlet 114 at a substantially opposite end of the funnel, cone, or the like.

In one embodiment, the water outlet 114 is in fluid communication with both the water collection opening 102 from an input side and a water storage reservoir 122 for collected water on an output side (e.g., through a tube 120, pipe 120, hose 120, conduit 120, and/or other channel 120). The water outlet 114 may be threaded, barbed, weldable/welded, and/or comprise another attachment mechanism for coupling the water outlet 114 to a tube 120, pipe 120, hose 120, conduit 120, and/or other channel 120 (e.g., with a waterproof seal, removable, and/or the like).

In one embodiment, the vertical adjustment mechanism 104 allows the water collection opening 102 to be moved and/or adjusted vertically (e.g., up and down) relative to a showerhead 118, water faucet 118, and/or other water source 118. For example, the vertical adjustment mechanism 104 may comprise a vertical post shaped for receipt by and/or coupling to a vertical sleeve, with a vertical locking mechanism 110 (e.g., a tab, a notch, a thumbscrew, a nut and bolt, a removable pin, a hook, or the like) that locks and/or secures the vertical post into the vertical sleeve. The vertical sleeve may be removably couplable and/or attachable to a wall near a showerhead 118, water faucet 118, and/or other water source 118, and/or directly to the showerhead 118, water faucet 118, and/or other water source 118 (e.g., to a pipe or the like).

In one embodiment, the horizontal adjustment mechanism 106 is configured to allow the water collection opening 102 to be placed at a plurality of different horizontal distances from a showerhead 118, water faucet 118, and/or other water source 118. For example, the horizontal adjustment mechanism 106 may provide a plurality of slots, each configured to receive pins, knobs, and/or other extensions from the water collection opening 102 to place the water collection opening 102 different horizontal distances/offsets away from the showerhead 118, water faucet 118, and/or other water source 118. In a further embodiment, the horizontal adjustment mechanism 106 may comprise one or more elongate tracks and/or slots along a length of the horizontal adjustment mechanism 106 along which the water collection opening 102 and/or the water outlet 114 may slide to different positions horizontally offset from the water source 118, until a user secures the angle locking mechanism 112 at a certain horizontal offset. In other embodiments, instead of or in addition to horizontal slots, tracks, or the like, the horizontal adjustment mechanism 106 may be telescoping, folding, or otherwise selectively extendable to different horizontal lengths from the showerhead 118, water faucet 118, and/or other water source 118.

In one embodiment, the angle locking mechanism 112 is configured to removably lock and/or secure the water collection opening 102 and/or the water outlet 114 to the horizontal adjustment mechanism 106 (e.g., at a user selectable position among different horizontal offsets relative to the water source 118, at a user selectable angle relative to the horizontal adjustment mechanism 106 and/or the water source 118, or the like). The angle locking mechanism 112 may adjustably lock and/or secure the water collection opening 102 and/or the water outlet 114 at a user selectable angle relative to the horizontal adjustment mechanism 106 and/or the water source 118. The angle locking mechanism 112, in various embodiments, may comprise a thumb screw, a bolt, a pin, a clamp, or the like.

In one embodiment, the radial adjustment mechanism 108 is configured to allow the horizontal adjustment mechanism 106 to rotate radially (e.g., within a horizontal plane) relative to the vertical adjustment mechanism 104 and/or to a showerhead 118, water faucet 118, and/or other water source 118. The radial adjustment mechanism 108 may allow the water collection opening 102 to be rotated and moved out of the way when not in use (e.g., after the shower water warms up, while lathering up, while shampooing hair, or the like), may allow the water collection opening 102 to be adjusted to fit a certain type, size, position, shape, and/or direction of showerhead 118, water faucet 118, and/or other water source 118, or the like.

The radial adjustment mechanism 108, in certain embodiments, may rotatably couple the horizontal adjustment mechanism 106 to an opposite end of the vertical adjustment mechanism 104 from the showerhead 118, water faucet 118, and/or other water source 118. For example, the radial adjustment mechanism 108 may allow the horizontal adjustment mechanism 106 to be radially rotatable around an axis of the radial adjustment mechanism 108 (e.g., to place the water collection opening 102 selectively in front of the water source 118 to capture a water stream, out of a water stream and to the side of the water source 118, or the like).

For example, in certain embodiments, the radial adjustment mechanism 108 may comprise a post, rod, shaft, hinge, joint, or the like to which the horizontal adjustment mechanism 106 is coupled, such that the horizontal adjustment mechanism 106 may selectively rotate around an axis of the radial adjustment mechanism 108. In one embodiment, a horizontal adjustment mechanism 106 includes a sleeve, opening, bushing, coupling, or the like configured to interface with and/or be coupled to a post, rod, shaft, hinge, joint, or the like of the radial adjustment mechanism 108, or the like.

In the depicted embodiment, the apparatus 100 includes one or more wall clips 132 configured to removably couple the water channel 120 (e.g., a tube 120, pipe 120, hose 120, conduit 120, and/or other water channel 120) to a wall of the shower 116. For example, a wall clip 132 may comprise a suction cup, adhesive, or the like on a first side, for coupling the wall clip 132 to a wall of the shower 116, and may comprise a loop, hook, clip, and/or other coupling mechanism configured to engage the water channel 120 on an opposite side (e.g., to guide the water channel 120 toward the water storage reservoir 122, to keep the water channel 120 out of the way in the shower 116, or the like). Similarly, one or more other wall clips 126 (e.g., suction cups, adhesive, or the like) may couple, stabilize, affix, or the like the vertical adjustment mechanism 104 and/or the horizontal adjustment mechanism 106 to a wall of the shower 116, or the like.

The water storage reservoir 122, in the depicted embodiment, comprises a bucket with a handle 128. A reservoir clip 130, in certain embodiments, may removably secure the water channel 120 (e.g., an end of the water channel 120 opposite the water outlet 114, or the like) to the water storage reservoir 122, directing water from the water channel 120 into the water storage reservoir 122, or the like.

Figure 2A:
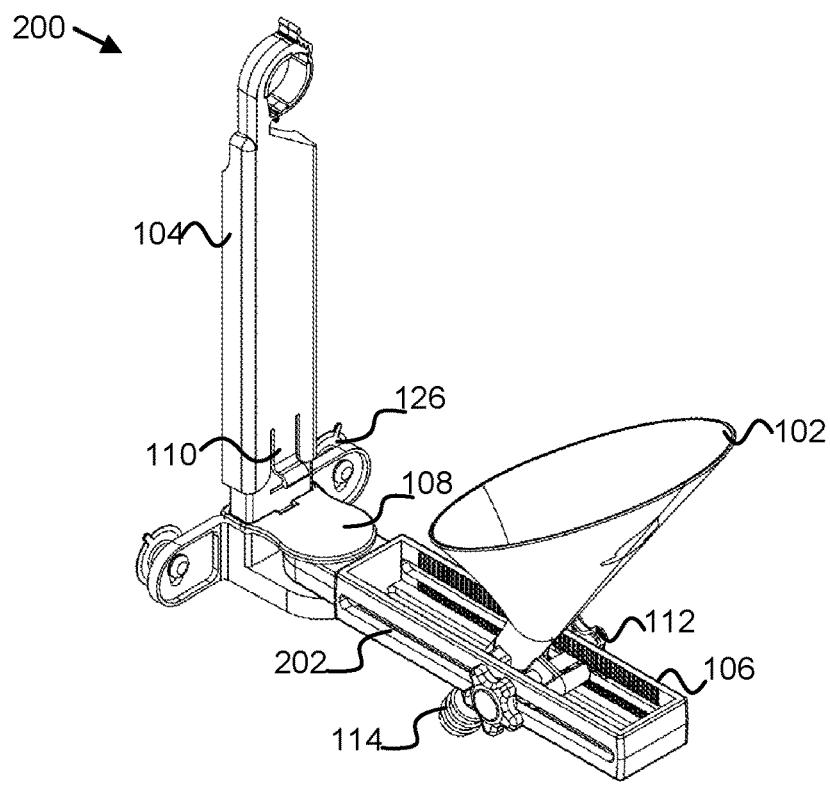
FIG. 2A is a schematic block diagram illustrating one embodiment of an adjustable apparatus for water capture.

FIG. 2A depicts one embodiment of an adjustable apparatus 200 for water capture. In the depicted embodiment, the apparatus 200 includes a horizontal adjustment mechanism 106 with two elongate slots 202 and/or tracks 202 along a length of the horizontal adjustment mechanism 106, along which the angle locking mechanism 114 may slide to a plurality of user selectable positions to removably couple the water collecting opening 102 and/or the water outlet 114 to the one or more elongate tracks 202 (e.g., as a user loosens the angle locking mechanism 114, slides the water collecting opening 102 along the elongate slots 202 and/or tracks 202, and tightens the angle locking mechanism 114, or the like).

Figure 2B:
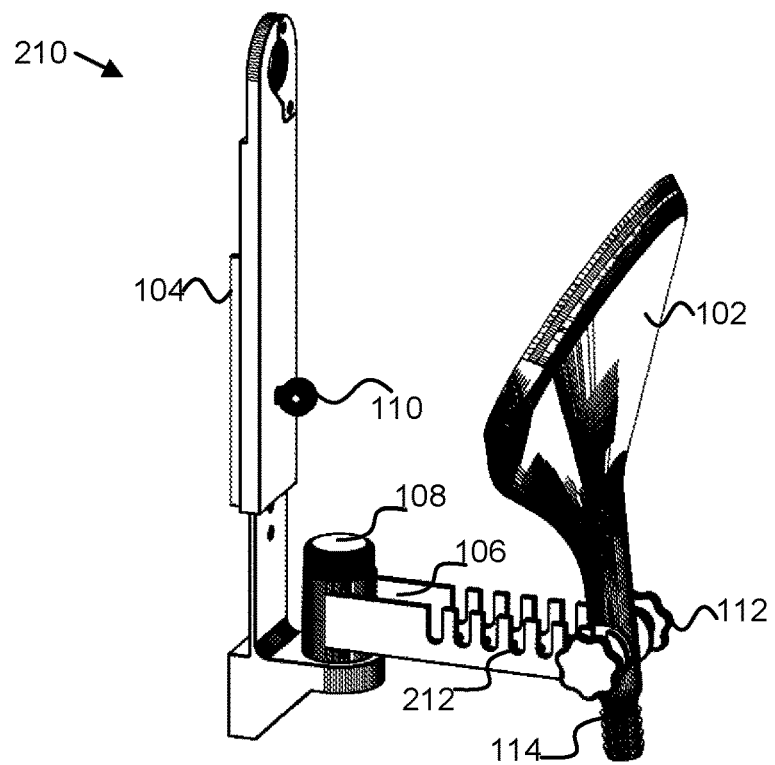
FIG. 2B is a schematic block diagram illustrating a further embodiment of an adjustable apparatus for water capture.

FIG. 2B depicts a further embodiment of an adjustable apparatus 210 for water capture. In the depicted embodiment, the apparatus 210 includes one or more notches 212 at each of a plurality of user selectable positions for the angle locking mechanism 114. The notches 212 may be shaped to receive the angle locking mechanism 114, which may be configured to removably couple the water collecting opening 102 and/or the water outlet 114 to a selected set of one or more notches 212 (e.g., in response to a user placing the angle locking mechanism 114 in the selected set of one or more notches 212 and tightening the angle locking mechanism 114, or the like).

Figure 3A:
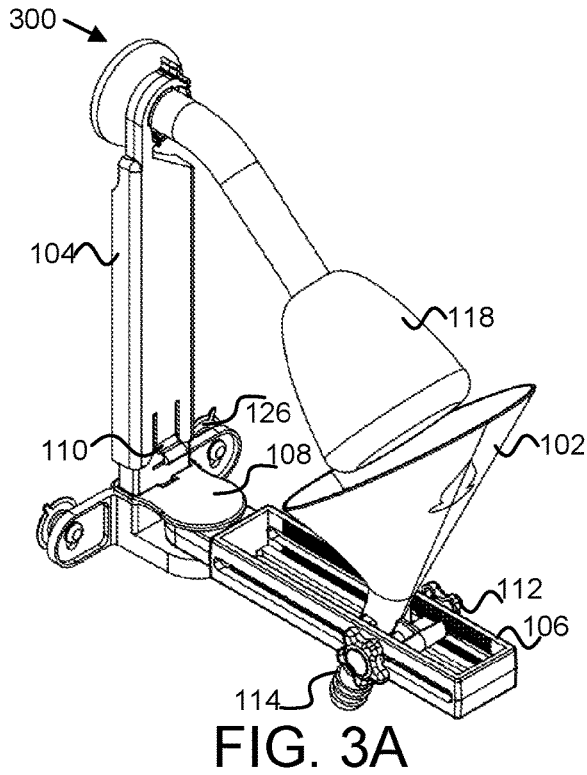
FIG. 3A is a schematic block diagram illustrating one embodiment of an adjustable apparatus for water capture adjusted to a first position.

FIG. 3A depicts one embodiment of an adjustable apparatus 300 for water capture adjusted to a first position. In the first position, in the depicted embodiment, the water collecting opening 102 is positioned in front of a water source 118 (e.g., a showerhead 118, or the like). For example, one or more of the vertical adjustment mechanism 104, the horizontal adjustment mechanism 106, the radial adjustment mechanism 108, and the angle locking mechanism 112 may be adjusted to place the water collecting opening 102 in the selected position relative to the water source 118.

Figure 3B:
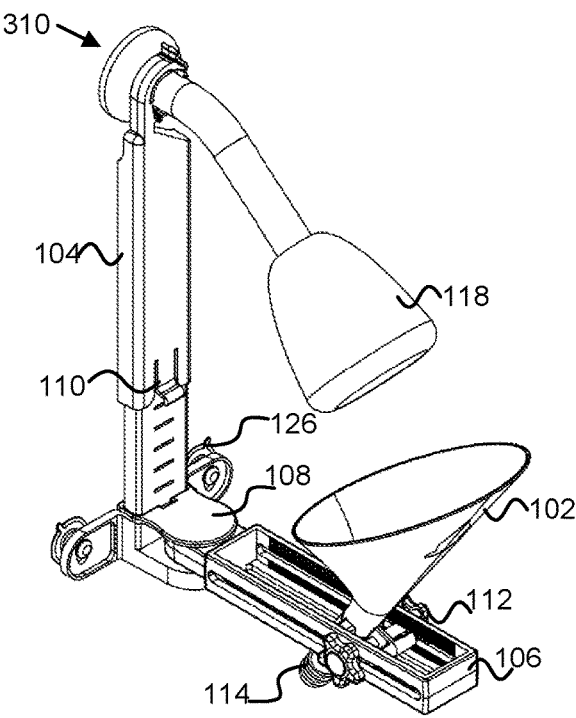
FIG. 3B is a schematic block diagram illustrating one embodiment of an adjustable apparatus for water capture adjusted to a second position.

FIG. 3B depicts one embodiment of an adjustable apparatus 310 for water capture adjusted to a second position. In the second position, in the depicted embodiment, the water collecting opening 102 has been lowered using the vertical adjustment mechanism 104, or the like, so that the water collecting opening 102 is lower relative to the water source 118 than in the first position of FIG. 3A. An angle of the water collecting opening 102, in certain embodiments, is adjusted in the second position using the angle locking mechanism 112.

Figure 3C:
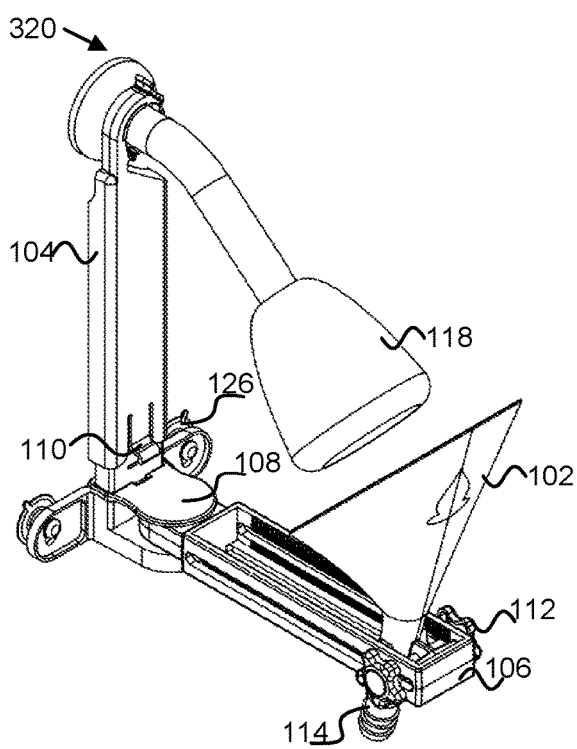
FIG. 3C is a schematic block diagram illustrating one embodiment of an adjustable apparatus for water capture adjusted to a third position.

FIG. 3C depicts one embodiment of an adjustable apparatus 320 for water capture adjusted to a third position. In the third position, in the depicted embodiment, the water collecting opening 102 has been adjusted to a distance further away, horizontally, from the water source 118, using the horizontal adjustment mechanism 104, or the like, so that the water collecting opening 102 has a greater horizontal distance from the water source 118 than in the first position of FIG. 3A.

Figure 3D:
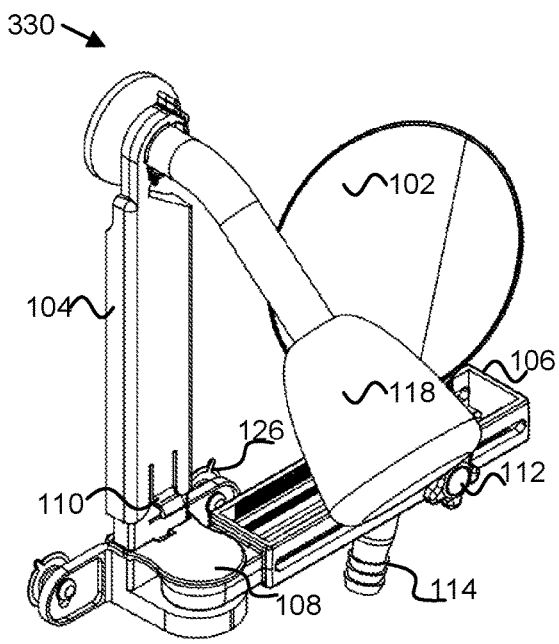
FIG. 3D is a schematic block diagram illustrating one embodiment of an adjustable apparatus for water capture adjusted to a fourth position.

FIG. 3D depicts one embodiment of an adjustable apparatus 330 for water capture adjusted to a fourth position. In the fourth position, in the depicted embodiment, the water collecting opening 102 has been rotated radially to a side of the water source 118, using the radial adjustment mechanism 108. For example, once water from the water source 118 has reached an acceptable temperature for a user, or the like, the user may rotate the water collecting opening 102 out of the way to continue with their shower, or the like.

Figure 4:
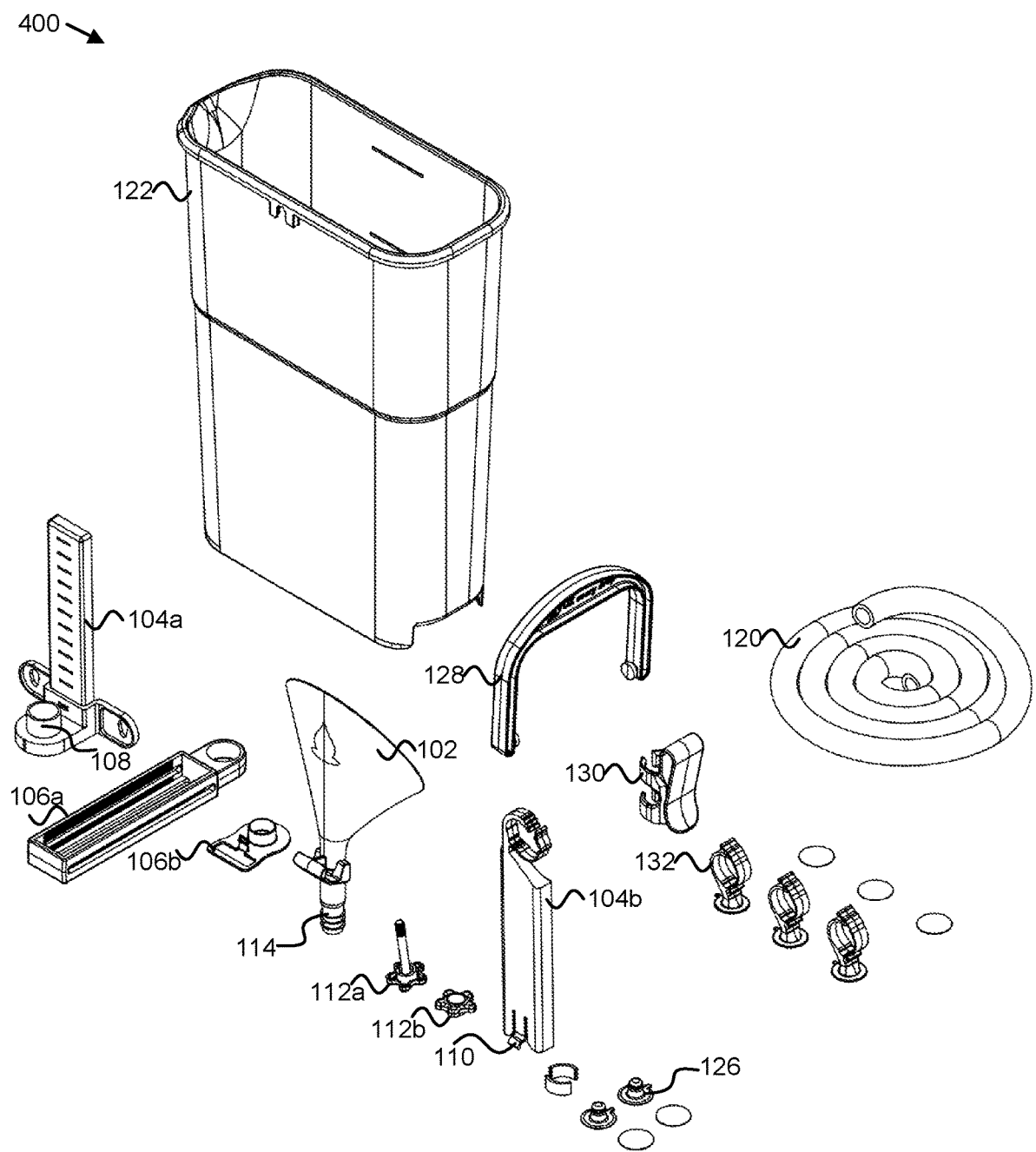
FIG. 4 is a schematic block diagram illustrating embodiments of components of an adjustable apparatus for water capture.

FIG. 4 depicts embodiments of components 400 of an adjustable apparatus for water capture. The components 400, in the depicted embodiment, may include a water collecting opening 102 with a water outlet 114 (e.g., in the shape of a funnel, cone, or the like), a vertical adjustment mechanism 104 (e.g., an inner vertical post 104a shaped to be received by, to slide into, and/or to be releasably coupled to a vertical sleeve 104b using a vertical locking mechanism 110, or the like), a horizontal adjustment mechanism 106 (e.g., a horizontal arm 106a, with an endcap 106b configured to couple the horizontal arm 106a to a radial adjustment mechanism 108, or the like), an angle locking mechanism 112 (e.g., a thumbscrew 112a and/or bolt 112a and a corresponding nut 112b and/or endcap 112b), a water channel 120, a water storage reservoir 122 with a handle 128, one or more wall clips 126, 132, a reservoir clip 130, and/or one or more other components 400.

Figure 5:
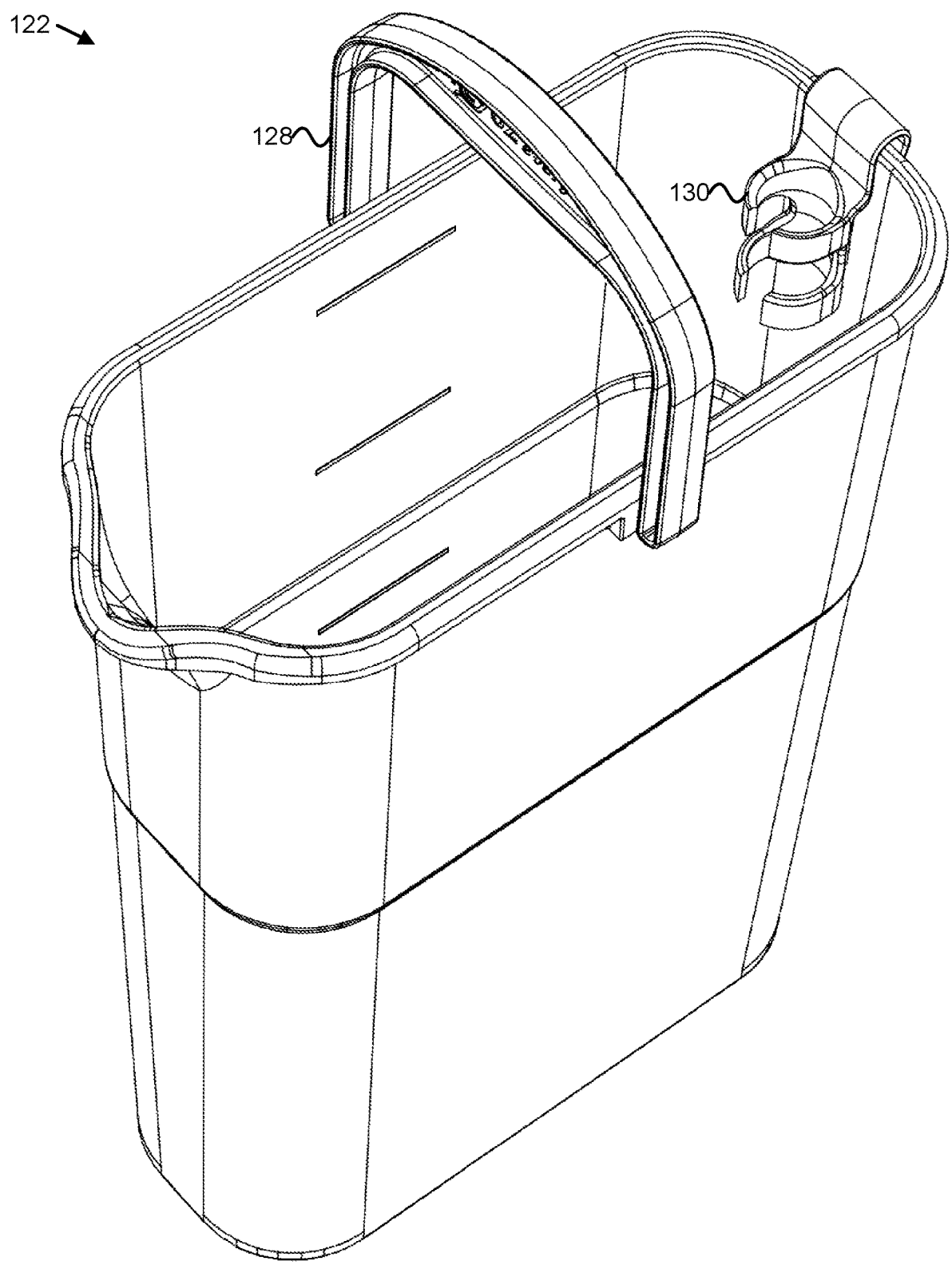
FIG. 5 is a schematic block diagram illustrating one embodiment of a water storage reservoir.

FIG. 5 depicts one embodiment of a water storage reservoir 122. In the depicted embodiment, the water storage reservoir 122 comprises a handle 128 and a reservoir clip 130, substantially as described above.

Figure 6:
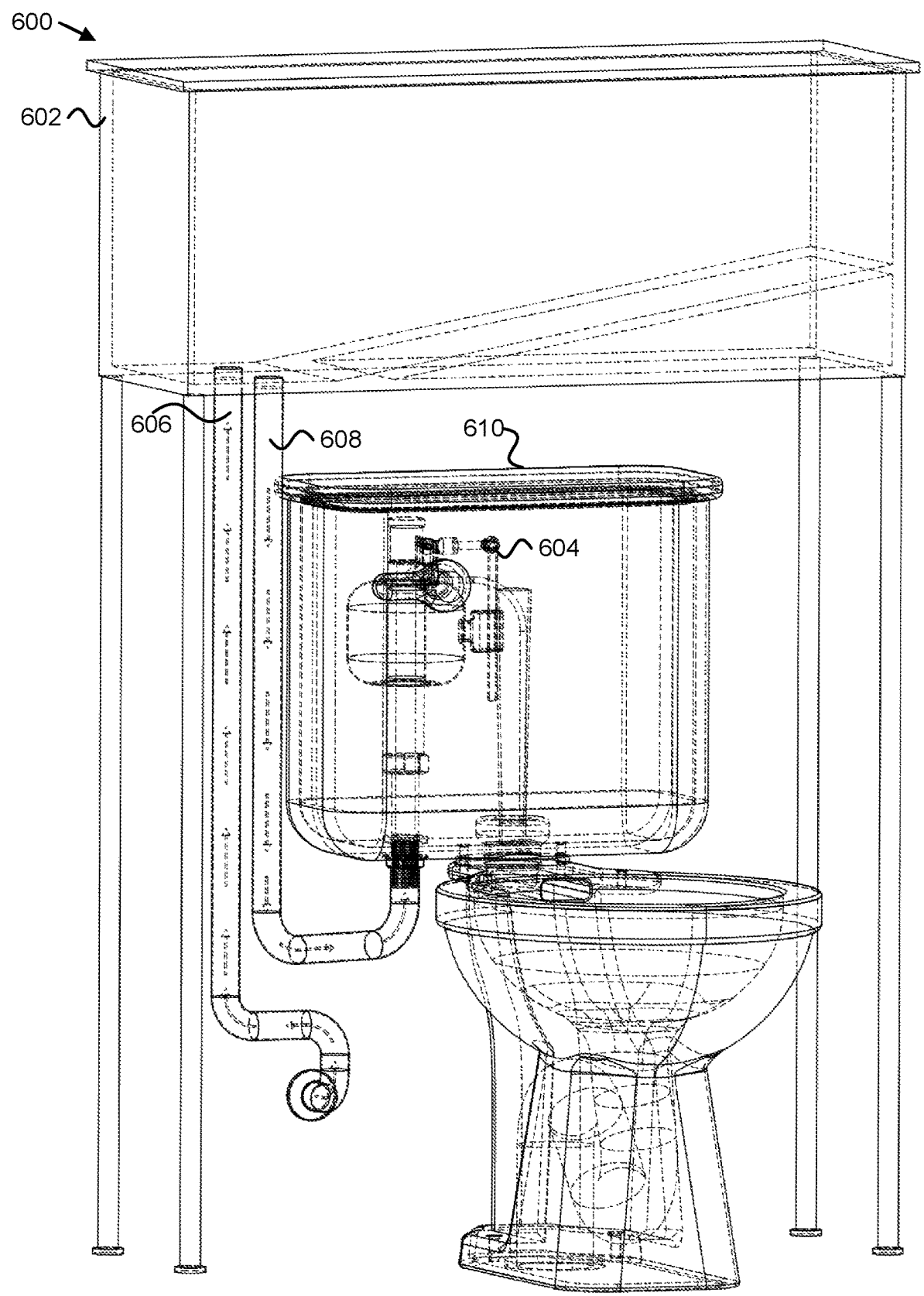
FIG. 6 is a schematic block diagram illustrating one embodiment of a toilet and a water storage reservoir.

FIG. 6 depicts one embodiment of a system 600 including a toilet 610 and a water storage reservoir 602. In the depicted embodiment, the system 600 includes a water storage reservoir 602, a fill controller 604, a water inlet line 606, and/or a water outlet line 608 for a toilet 610. The system 600, in certain embodiments, allows reclaimed and/or captured water from a water outlet 114 as described above to be used to flush a toilet 610, or the like. In other embodiments, instead of and/or in addition to being disposed adjacent to or near a toilet 610, the water storage reservoir 602 may be disposed within a shower 116 with an adjustable apparatus for water capture or the like (e.g., against a wall under one or more shower valve handles, in a corner of the shower 116, and/or otherwise out of the way).

In one embodiment, the water storage reservoir 602 is configured to receive water directly from the water outlet 114, water indirectly from the water outlet 114 manually poured by a user, and/or water from a municipal or utility potable water source (e.g., through a building's plumbing), or the like, and to provide the received water through the water outlet line 208 to flush a toilet 610. For example, a fill controller 604 (e.g., a float mechanism or the like) may fill a tank of the toilet 610 with water from the water storage reservoir 602, and/or from a potable water source if water from the water storage reservoir 602 is not available, is not sufficient, or the like.

In another embodiment, the water storage reservoir 602 may comprise a fill controller 604 configured to fill the water storage reservoir 602 up to a lower amount (e.g., about 1.5 gallons or the like) from a potable water source (e.g., through a building's plumbing via the water inlet line 606), and may fill and/or allow a user to fill the water storage reservoir 602 to a greater amount (e.g., about 4 gallons or the like) from an adjustable apparatus for water capture. In this manner, in certain embodiments, a fill controller 604 may allow the water storage reservoir 602 to use recovered gray water for flushing the toilet 610, when available, before using potable water.

Figure 7:
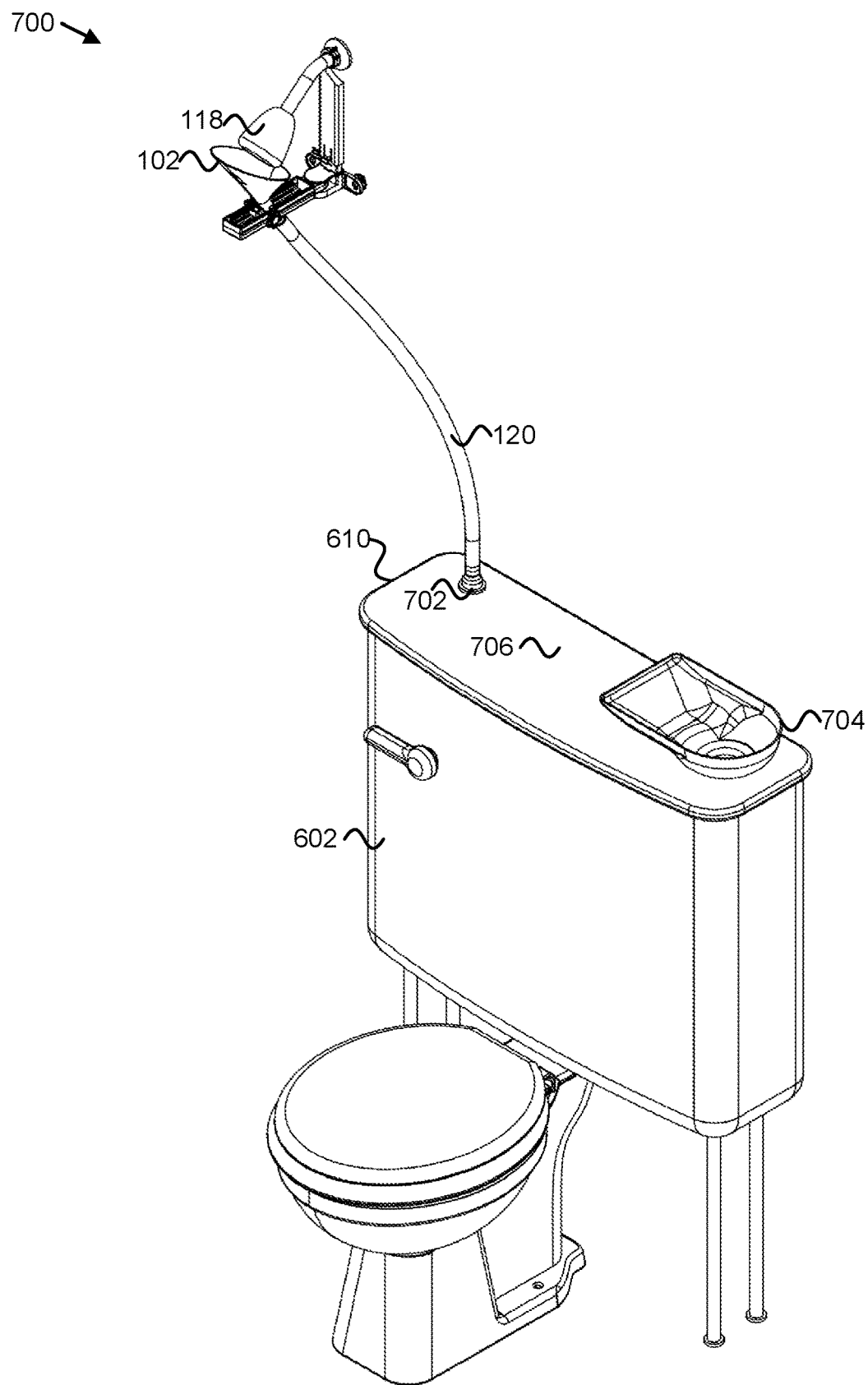
FIG. 7 is a schematic block diagram illustrating one embodiment of a system comprising an adjustable apparatus for water capture and a water storage reservoir.

FIG. 7 depicts one embodiment of a system 700 comprising an adjustable apparatus for water capture and a water storage reservoir 602. In the depicted embodiment, the water storage reservoir 602 comprises a toilet tank, and a lid 706 of the toilet 610 includes a first inlet 702 (e.g., an inlet port with threads, barbs, or the like to engage an end of the water channel 120) to which the water channel 120 is coupled to deliver collected water from the water source 118 into the toilet tank 602. The lid 706 of the toilet tank 602, in the depicted embodiment, also includes a second inlet 704 shaped for a user to poor water from another water storage reservoir 602 (e.g., a bucket 602 or the like) into the toilet tank 602 through the second inlet 704. For example, the second inlet 704 may be shaped like a funnel, a cone, or the like with a wider opening outward from the lid 706 than an outlet through the lid 706 into the toilet tank 602, or the like.

Figure 8:
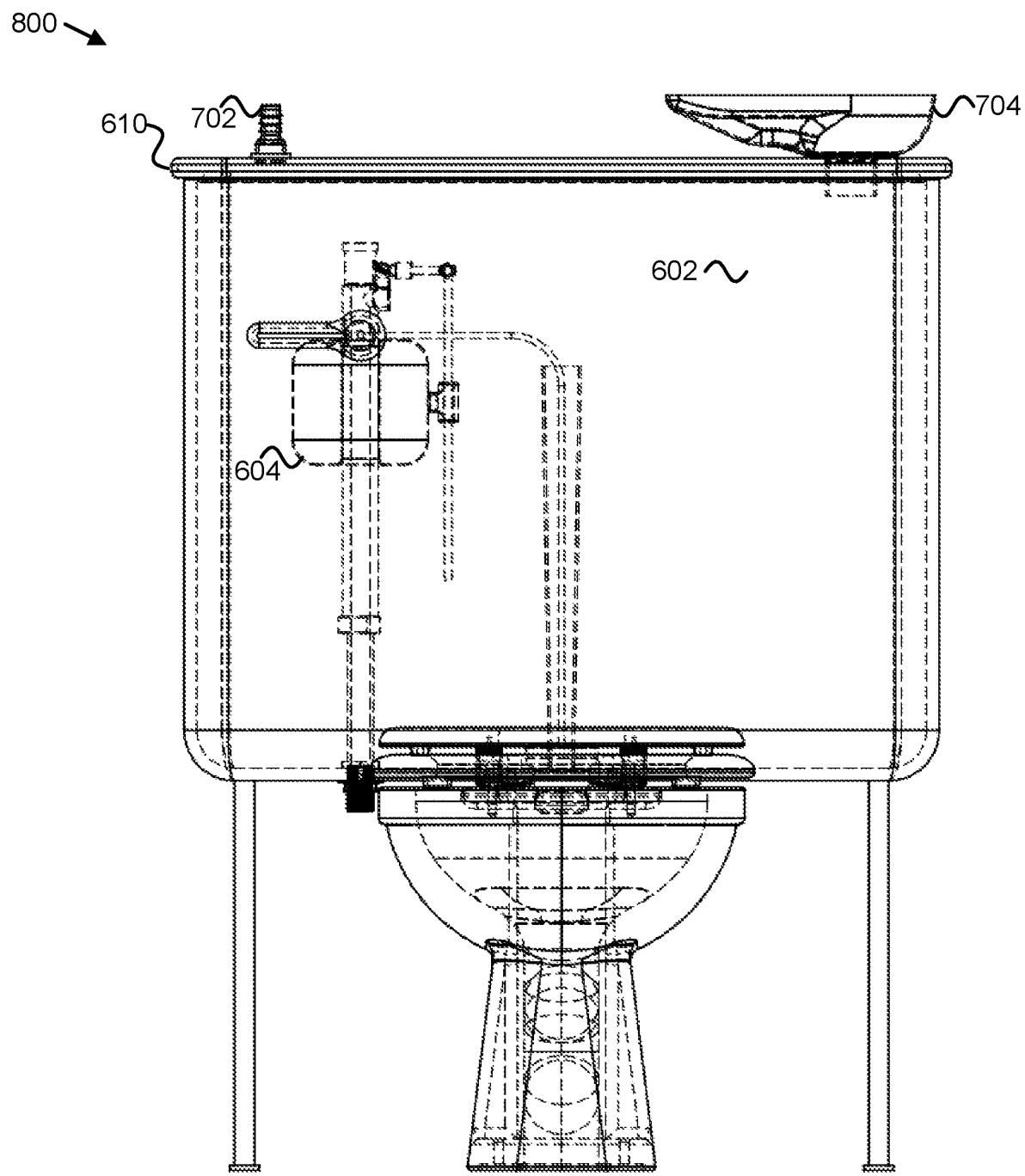
FIG. 8 is a schematic block diagram illustrating one embodiment of a water storage reservoir for a toilet.

FIG. 8 depicts one embodiment of a system 800 with a water storage reservoir 602 for a toilet 610. The system 800, in the depicted embodiment, may be substantially similar to the system 700 of FIG. 7, with a fill controller 604 within the toilet tank 602, as described above with regard to FIG. 6. The toilet tank 602, in certain embodiments, may be larger than a traditional toilet tank, but with a similar or smaller flush volume (e.g., to conserve water). For example, the toilet tank 602 may have a water storage capacity multiple times (e.g., at least two times) larger than a flush volume of the toilet 610, in order to store as much collected water (e.g., gray water) from the water source 118 as possible, or the like.

A means for collecting water from a water source 118, in various embodiments, may include a water collecting opening 102, a water outlet 114, a water channel 120, a water storage reservoir 122, 602, an inlet 702, 704, a toilet tank 602, a toilet 610, a funnel, a cone, a hose, a pipe, a conduit, a tube, or the like. Other embodiments may include similar or equivalent means for collecting water from a water source 118.

A means for storing collected water from a water source 118 for reuse, in various embodiments, may include a water collecting opening 102, a water outlet 114, a water channel 120, a water storage reservoir 122, 602, an inlet 702, 704, a toilet tank 602, a toilet 610, a bucket, a barrel, a can, a bag, or the like. Other embodiments may include similar or equivalent means for storing collected water from a water source 118.

A means for providing mechanical support to a means for collecting water at any one of a plurality of user selectable positions at different horizontal offsets relative to a water source 118 to accommodate different sizes and/or types of water sources 118, in various embodiments, may include a horizontal adjustment mechanism 104, an angle locking mechanism 108, one or more slots 202 and/or tracks 202, one or more notches 212 or other openings, an extension, an arm, a bar, a rod, or the like. Other embodiments may include similar or equivalent means for providing mechanical support.

A means for providing mechanical support to a means for collecting water at any one of a plurality of user selectable positions at different vertical offsets relative to a water source 118 to accommodate the different sizes and/or types of water sources 118, in various embodiments, may include a vertical adjustment mechanism 104, an inner vertical post 104a, a vertical sleeve 104b, a vertical locking mechanism 110, an angle locking mechanism 108, a hook, a latch, a fastener, or the like. Other embodiments may include similar or equivalent means for providing mechanical support.

A means for radially rotating a means for collecting water around a water source 118 to place a water collection opening 102 selectively in front of the water source 118 and/or to one or more other sides of the water source 118, in various embodiments, may include a radial adjustment mechanism 108, a horizontal adjustment mechanism 106, a vertical adjustment mechanism 104, an angle locking mechanism 108, one or more slots 202 and/or tracks 202, one or more notches 212 or other openings, a post, a rod, a shaft, a hinge, a joint, or the like. Other embodiments may include similar or equivalent means for rotating.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An apparatus comprising:
   a water collection opening shaped to collect water from a water source;
   a water outlet in fluid communication with the water collection opening to receive collected water from the water source through the water collection opening;
   a horizontal adjustment mechanism configured to provide mechanical support to the water outlet and the water collection opening at any one of a plurality of user selectable positions at different horizontal offsets relative to the water source to accommodate different sizes and types of water sources; and
   a vertical adjustment mechanism configured to engage the water source on one end of the vertical adjustment mechanism, the horizontal adjustment mechanism extending from an opposite end of the vertical adjustment mechanism.

2. The apparatus of claim 1, wherein the vertical adjustment mechanism is configured to provide mechanical support to the water outlet, the water collection opening, and the horizontal adjustment mechanism at any one of a plurality of user selectable positions at different vertical offsets relative to the water source to accommodate the different sizes and types of water sources.

3. The apparatus of claim 1, further comprising a radial adjustment mechanism configured to rotatably couple the horizontal adjustment mechanism to the opposite end of the vertical adjustment mechanism such that the horizontal adjustment mechanism is radially rotatable around an axis of the radial adjustment mechanism to place the water collection opening selectively in front of the water source and to one or more other sides of the water source.

4. The apparatus of claim 1, further comprising an angle locking mechanism configured to removably couple one or more of the water collecting opening and the water outlet to any one of the plurality of user selectable positions along a length of the horizontal adjustment mechanism.

5. The apparatus of claim 4, wherein the angle locking mechanism is further configured to removably lock the water collecting opening at a user selectable angle relative to the horizontal adjustment mechanism.

6. The apparatus of claim 4, wherein the horizontal adjustment mechanism comprises one or more elongate tracks along a length of the horizontal adjustment mechanism along which the angle locking mechanism is configured to slide to the plurality of user selectable positions, the angle locking mechanism configured to removably couple the one or more of the water collecting opening and the water outlet to the one or more elongate tracks.

7. The apparatus of claim 4, wherein the horizontal adjustment mechanism comprises one or more notches at each of the plurality of user selectable positions, the notches shaped to receive the angle locking mechanism and the angle locking mechanism configured to removably couple the one or more of the water collecting opening and the water outlet to the notches.

8. The apparatus of claim 1, further comprising a water channel and a water storage reservoir, wherein one end of the water channel is coupled to the water outlet and another end of the water channel delivers the collected water from the water outlet to the water storage reservoir.

9. The apparatus of claim 8, wherein the water storage reservoir comprises a bucket.

10. The apparatus of claim 8, wherein the water storage reservoir comprises a toilet tank and a lid of the toilet tank comprises an inlet to which the water channel is coupled to deliver the collected water from the water source into the toilet tank.

11. The apparatus of claim 10, wherein the lid of the toilet tank comprises a second inlet shaped for a user to poor water from another water storage reservoir into the toilet tank through the second inlet.

12. The apparatus of claim 10, wherein the toilet tank has a water storage capacity multiple times larger than a flush volume of a toilet in fluid communication with the toilet tank.

13. The apparatus of claim 1, wherein the water collection opening comprises a concave chamber with an opening facing toward the water outlet when the water collection opening is installed on the horizontal adjustment mechanism.

14. The apparatus of claim 1, wherein the water source comprises a showerhead installed in a shower.

15. A system comprising:
a conical water collection opening positionable to collect water from a showerhead;
a water outlet in fluid communication with the conical water collection opening and receiving collected water from the showerhead through the conical water collection opening;
a horizontal adjustment mechanism providing mechanical support to the water outlet and the conical water collection opening at any one of a plurality of user selectable positions at different horizontal offsets relative to the showerhead;
a vertical adjustment mechanism coupled to the water source on one end of the vertical adjustment mechanism, the horizontal adjustment mechanism extending from an opposite end of the vertical adjustment mechanism; and
a radial adjustment mechanism configured to rotatably couple the horizontal adjustment mechanism to an opposite end of the vertical adjustment mechanism such that the horizontal adjustment mechanism is radially rotatable around an axis of the radial adjustment mechanism.

16. The system of claim 15, further comprising an angle locking mechanism configured to removably couple one or more of the conical water collecting opening and the water outlet to any one of the plurality of user selectable positions along a length of the horizontal adjustment mechanism.

17. An apparatus comprising:
means for collecting water from a water source;
means for storing the collected water from the water source for reuse;
means for providing mechanical support to the means for collecting the water at any one of a plurality of user selectable positions at different horizontal offsets relative to the water source to accommodate different sizes and types of water sources; and
means for radially rotating the means for collecting water around the water source to place the water collection opening selectively in front of the water source and to one or more other sides of the water source.

18. The apparatus of claim 17, further comprising means for providing mechanical support to the means for collecting water at any one of a plurality of user selectable positions at different vertical offsets relative to the water source to accommodate the different sizes and types of water sources.

* * * * *